(12) United States Patent
Spataro et al.

(10) Patent No.: US 11,408,521 B2
(45) Date of Patent: Aug. 9, 2022

(54) PRESSURE-DRIVEN FLOW RATE CONTROL VALVES

(71) Applicant: Becton, Dickinson and Company, Franklin Lakes, NJ (US)

(72) Inventors: Joseph Spataro, Cottonwood Heights, UT (US); Curtis H. Blanchard, Riverton, UT (US); Megan Scherich, Salt Lake City, UT (US); Weston F. Harding, Lehi, UT (US); Jonathan Karl Burkholz, Salt Lake City, UT (US); Bin Wang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/081,919

(22) Filed: Oct. 27, 2020

(65) Prior Publication Data
US 2021/0140550 A1 May 13, 2021

Related U.S. Application Data (60) Provisional application No. 62/934,956, filed on Nov. 13, 2019.

(51) Int. Cl.
| | | |
|---|---|---|
| G05D 7/01 | (2006.01) | |
| F16K 15/02 | (2006.01) | |
| F16K 15/16 | (2006.01) | |
| F16K 15/03 | (2006.01) | |

(52) U.S. Cl.
CPC .......... *F16K 15/021* (2013.01); *F16K 15/026* (2013.01); *F16K 15/03* (2013.01); *F16K 15/16* (2013.01); *G05D 7/012* (2013.01); *G05D 7/0133* (2013.01)

(58) Field of Classification Search
CPC ......... Y10T 137/2584; Y10T 137/2615; Y10T 137/7727; Y10T 137/7728; G05D 7/012
USPC ..................................................... 138/45, 46
See application file for complete search history.

(56) References Cited

U.S. PATENT DOCUMENTS

| | | | | |
|---|---|---|---|---|
| 2,829,674 | A * | 4/1958 | Segelhorst | G05D 7/012 138/45 |
| 3,326,242 | A * | 6/1967 | Parkison | B64C 27/20 138/46 |
| 4,191,204 | A * | 3/1980 | Nehring | A61M 1/74 137/205 |
| 4,609,014 | A * | 9/1986 | Jurjevic | G05D 7/012 137/504 |
| 10,557,560 | B2 * | 2/2020 | Gandikota | F15D 1/025 |
| 2009/0254049 | A1 | 10/2009 | Adams | |
| 2010/0217209 | A1 | 8/2010 | Meng et al. | |
| 2012/0024987 | A1 | 2/2012 | Naegele | |
| 2013/0081726 | A1 | 4/2013 | Oh | |
| 2014/0194851 | A1 | 7/2014 | Burke et al. | |
| 2018/0339141 | A1 | 11/2018 | Scheule et al. | |
| 2019/0282150 | A1 | 9/2019 | Russ et al. | |

* cited by examiner

*Primary Examiner* — Kevin F Murphy
(74) *Attorney, Agent, or Firm* — The Webb Law Firm (57) ABSTRACT

A storage container having a base storage compartment configured to receive a divider by which the storage compartment is divided into two or more sub-compartments, wherein divider includes a tool configured to provide a secondary utility or function unrelated to dividing the storage compartment.

7 Claims, 11 Drawing Sheets

PRESSURE-DRIVEN FLOW RATE CONTROL VALVES

RELATED APPLICATIONS

This application claims the benefit of U.S. Provisional Application No. 62/934,956, filed Nov. 13, 2019, and entitled PRESSURE-DRIVEN FLOW RATE CONTROL VALVES, which is incorporated herein in its entirety.

FIELD OF THE INVENTION

This invention generally relates to valves for use in systems configured to collect or dispense fluids at a desired flow rate. In particular, this invention relates to control valves comprising various components configured to maintain a desired flow rate, and/or prevent the occurrence of an undesirable flow rate. Control valves of the present invention may be incorporated into a variety of devices for use with fluids that are sensitive to flow rates, such as biological liquids comprising live cells, shear-sensitive fluids, emulsions, and chemically unstable fluids.

BACKGROUND OF THE INVENTION

There are many instances where it is desirable to transfer a fluid that is sensitive to flow rate. In these instances it is imperative that a safe flow rate for the fluid be maintained while transferring the fluid. Failure to do so may compromise the quality of the fluid. In instances where the fluid is required for medical treatment or diagnostics, failure to maintain a safe flow rate could result in misdiagnosis, lost time and resources, delayed treatment, serious injury, and potentially death.

In the healthcare setting, clinicians frequently draw blood from patients immediately after a successful catheter insertion. Often these blood samples are collected using a vacuum container, wherein a vacuum pressure within the vacuum container is configured to draw blood into the container as soon as the container is connected to an intravenous access device. Vacuum containers are not designed for use with intravenous catheters, but are rather designed for use with intravenous needles wherein the diameter of the fluid pathway of the intravenous needle is generally greater than that of the intravenous catheter. In some instances, vacuum containers are incompatible for use with intravenous catheter lines. For example, a vacuum pressure of a vacuum container may draw the blood sample through the intravenous catheter at a flow rate that damages the live blood cells. Alternatively, a vacuum pressure may be insufficient for a particular intravenous catheter, whereby the fill time is unnecessarily prolonged.

In many instances, a clinician opts to extract blood from a patient's intravenous catheter using a manual syringe. The syringe offers a level of control over the draw that automated vacuum containers cannot match. While use of a syringe enhances control opportunities over the draw, sample quality may suffer if a clinician introduces a significant vacuum to reduce fill time.

Thus, while systems and methods currently exist for collecting or dispensing fluids at a desired flow rate, challenges still exist. The present invention addresses and overcomes these challenges.

BRIEF SUMMARY OF THE INVENTION

This invention generally relates to valves for use in systems configured to collect or dispense fluids at a desired flow rate. In particular, this invention relates to control valves comprising various components configured to maintain a desired flow rate, and/or prevent the occurrence of an undesirable flow rate. Control valves of the present invention may be incorporated into a variety of devices for use with fluids that are sensitive to flow rates, such as biological liquids comprising live cells, shear-sensitive fluids, emulsions, and chemically unstable fluids.

In some instances, the present invention provides a valve for controlling flow of a fluid at a desired flow rate, wherein said valve comprises an enclosure comprising an inlet and an outlet; a primary fluid path; and a septum positioned within an interior of the enclosure and in proximity to the primary fluid path, the septum comprising a first configuration at a first fluid pressure within the interior, and a second configuration at a second fluid pressure within the interior. In some instances, the septum further comprises a fluid pressure threshold at which the septum switches from the first configuration to the second configuration. In some instances, the first configuration is an opened configuration. In some instances, the first fluid pressure is equal to, or less than the fluid pressure threshold. In some instances, the second configuration is a closed configuration. In some instances, the second fluid pressure is greater than the fluid pressure threshold.

In some aspects of the invention, a fluid pressure threshold is a fluid vacuum pressure threshold, wherein a vacuum pressure is applied to an output end of the valve. In some aspects of the invention, a first fluid pressure is a first fluid vacuum pressure, and a second fluid pressure is a second fluid vacuum pressure.

In some instances, a first configuration of a septum is an open configuration, and a first fluid vacuum pressure experienced by the septum is less than or equal to a fluid vacuum pressure threshold of the septum. In some instances, a second configuration of the septum is a closed configuration, and a second fluid vacuum pressure experience by the septum is greater than a fluid vacuum pressure threshold of the septum.

In some embodiments, a septum of the present invention comprises an aperture. In some instances, when the septum is in a first configuration, the aperture of the septum is opened, and when in the second configuration the aperture is closed. In some embodiments, when the septum is in the first configuration the aperture of the septum is closed, and when in the second configuration the aperture is opened. In some embodiments, an aperture of the septum comprises at least one of the primary fluid path and a secondary fluid path of the valve.

In some instances, an aperture of a septum is opened to a first width in a first configuration of the septum, and reduced to a second width in a second configuration of the septum, wherein the second width reduces a fluid flow or a rate of fluid flow through the aperture. In some embodiments, the second width of the aperture entirely prevents a fluid flow through the aperture and/or the valve.

In some aspects of the invention, a primary fluid path of the valve is unobstructed when the septum is in a first configuration, and obstructed when the septum is in a second configuration. In some instances, contact between the septum and an interior surface of the valve enclosure obstructs the primary fluid path. In some instances, contact between opposing surfaces of the septum, including, but not limited to opposing surfaces of an aperture of the septum, obstructs the primary fluid path of the valve. In some instances, a secondary fluid path of the valve is unobstructed by the septum when the septum is in a second configuration. In some instances, a secondary fluid path of the valve is unobstructed by the septum when the septum is in a first configuration.

In some embodiments, a septum of the present invention comprises the secondary fluid path. In some instances, a septum of the present invention comprises a primary fluid path and a secondary fluid path. In some instances, a primary fluid path of the septum comprises a primary flow rate capacity that is greater than a secondary flow rate capacity of a secondary fluid path.

In some instances, a septum of the present invention is fixedly positioned within an interior of a valve. In some instances, a septum of the present invention is movable positioned within the interior of a valve.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1A:
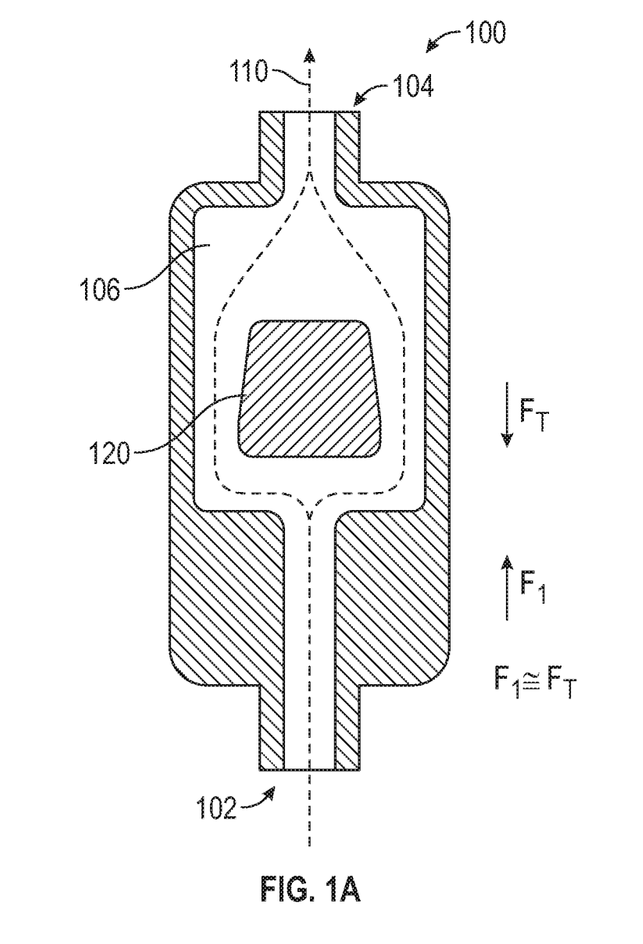
FIG. 1A is a cross-section view of a valve for controlling flow of a fluid, wherein the valve is shown in an open configuration in accordance with a representative embodiment of the present invention.

Referring now to FIG. 1, a valve 100 for controlling the flow of a fluid is shown. Valve 100 generally comprises an enclosure having an inlet 102, an outlet 104, and an interior 106 interposed therebetween. Valve 100 may comprise any structural form, shape, dimension, or size as may be desired. In some embodiments, valve 100 comprises an in-line component, wherein inlet 102 is coupled to an upstream fluid line, and outlet 104 is coupled to a downstream fluid line, such that a fluid flows through a primary fluid path 110 of the valve. In some embodiments, valve 100 is incorporated into a fluid handling component, such as an intravenous catheter, a catheter adapter, a vacuum container, luer connector, or the like, wherein the features of the present invention are incorporated in such a way that a fluid flows through a primary fluid path 110 of the valve. In some embodiments, valve 100 is incorporated into a secondary component of a fluid line, such as a filter or a fluid pump.

Valve 100 may comprise any material compatible for use with a desired fluid. In some embodiments, valve 100 comprises a polymer material. In some embodiments, valve 100 comprises a metal material. In some embodiments, valve 100 comprises a rigid material. In some embodiments, valve 100 comprises a semi-rigid or semi-flexible material. In some embodiments, valve 100 comprises a flexible material.

Valve 100 further comprise a septum 120 or other compatible element (such as, for example, a piston) disposed within interior 106 and in proximity to the primary fluid path 110. In some embodiments, a position of septum 120 in interior 106 is fixed. In some embodiments, septum 120 is movably positioned within interior 106. For example, in some embodiments septum 120 may slide forward and/or backwards towards inlet 102 and outlet 104. In a further example, septum 120 may be pivotally coupled to interior 106, such that septum 120 may move between vertical and horizontal positions. In some embodiments, septum 120 is free to move within interior 106, such as due to the force of gravity, and/or due to a fluid pressure or a vacuum fluid pressure within interior 106. In some embodiments, movement of septum 120 within interior 106 is controlled or otherwise limited, such as by a tether or a biasing element. Septum 120 may comprise any material compatible for use with a desired fluid. In some embodiments, septum 120 comprises a polymer material. In some embodiments, septum 120 comprises a metal material. In some embodiments, septum 120 comprises a rigid material. In some embodiments, septum 120 comprises a semi-rigid or semi-flexible material. In some embodiments, septum 120 comprises a flexible material.

In some embodiments, septum 120 comprises a fluid pressure threshold ($f_T$) at which septum 120 changes from a first configuration to a second configuration. As used herein, the term "fluid pressure threshold" refers to fluid pressure limit of septum 120. When a fluid pressure experienced by septum 120 is less than or, in some instances, approximately equal to the fluid pressure threshold of septum 120, septum 120 assumes and/or maintains a first configuration. However, when a fluid pressure experienced by septum 120 is equal to or greater than the fluid pressure threshold of septum 120, septum 120 assumes, transforms, or changes to a second configuration. As used herein, and as applied to the various embodiments of the present invention, the term "fluid pressure" may refer to positive fluid pressure, and/or vacuum fluid pressure. In some embodiments, a "fluid pressure threshold" of septum 120 may alternatively describe a flow rate limit of septum 120, wherein when a flow rate experienced by septum 120 is less than a flow rate limit of septum 120, septum 120 assumes and/or maintains a first configuration, and wherein when a flow rate experienced by septum 120 is equal to or greater than a flow rate limit of septum 120, septum 120 assumes, transforms, or changes to a second configuration.

The fluid pressure threshold of a septum may be achieved through design of the septum and/or other components of the valve comprising the septum. For example, fluid dynamics may be used to increase or decrease the septum's drag while in the primary fluid path, wherein drag may increase or decrease the septum's fluid pressure threshold. Similarly, fluid dynamics may be used to increase or decrease flow efficiencies of the primary fluid path. Where the valve comprises an intended orientation, the mass of the septum may be selected to match a desired flow rate and/or fluid pressure.

Figure 1B:
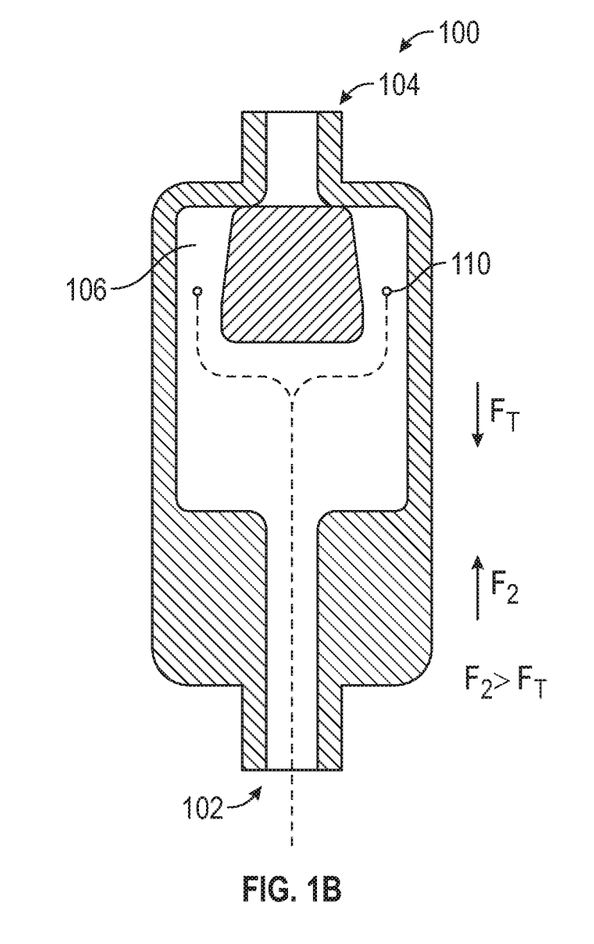
FIG. 1B is the valve of FIG. 1A, wherein the valve is shown in a closed configuration in accordance with a representative embodiment of the present invention.

With continued reference to FIG. 1A, septum 120 is shown in a first configuration wherein a primary fluid path 110 is open between inlet 120 and outlet 140. In some embodiments, valve 100 is oriented parallel to the Earth's gravitational force, whereby the fluid pressure threshold of septum 120 is equal and opposite to the Earth's gravitational force on septum 120. When septum 120 experiences a first fluid pressure ($f_1$) that is approximately equal to the Earth's gravitational force on septum 120, a first configuration of septum 120 is maintained, whereby the primary fluid path 110 is open (i.e., the inlet 102 and outlet 104 are in fluid communication with the primary fluid path 110). As used herein, the term "first fluid pressure" refers to a desired, compatible fluid pressure for a fluid that is sensitive to flow rates and/or fluid pressures. When septum 120 experiences a second fluid pressure ($f_2$) that is greater than the fluid pressure threshold of septum 120 (i.e., the Earth's gravitational force on septum 120), the fluid pressure threshold is overcome and septum 120 assumes a second configuration, wherein septum 120 occludes and closes the primary fluid path 110, as shown in FIG. 1B. As used herein, the term "second fluid pressure" refers to an undesired, non-compatible fluid pressure for a fluid that is sensitive to flow rates and/or fluid pressures. For this embodiment, the second configuration of septum 120 prevents all fluid flow through valve 100. Upon reduction of the second fluid pressure, septum 120 resumes the first configuration, thereby reopening the primary fluid path 110.

Figure 2A:
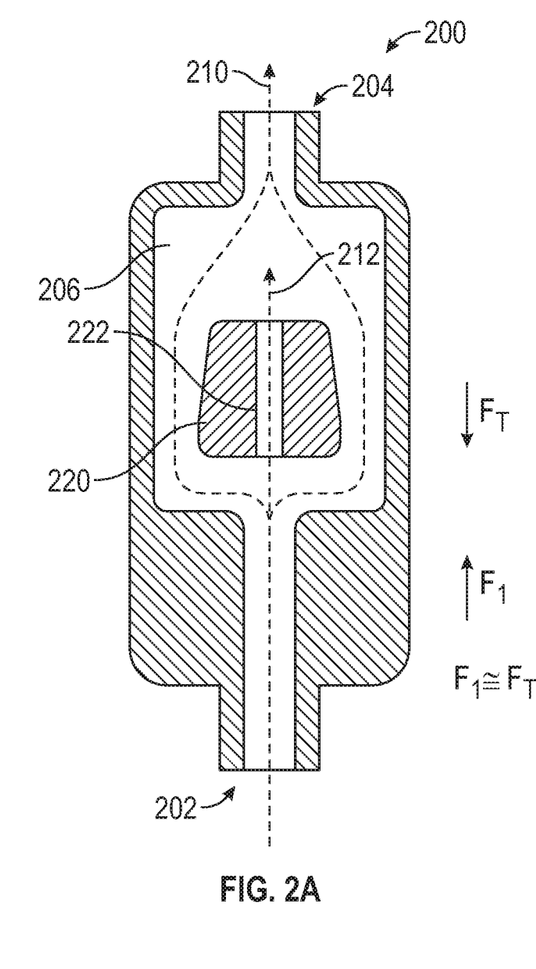
FIG. 2A is a cross-section view of a valve for controlling flow of a fluid, wherein the valve is shown in a first configuration in which a first fluid path and a second fluid path of the valve are open in accordance with a representative embodiment of the present invention.
Figure 2B:
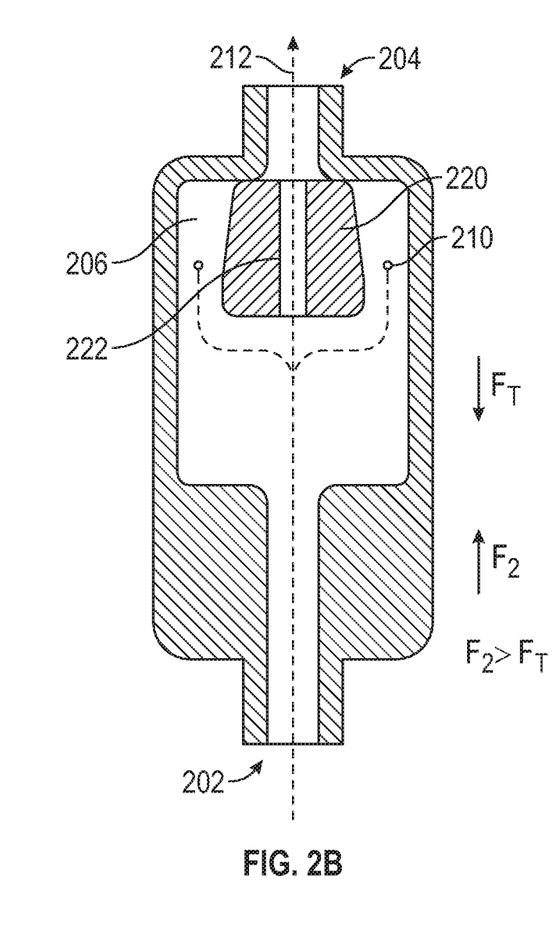
FIG. 2B is the valve of FIG. 2A, wherein the valve is shown in a second configuration in which the first fluid path is closed, and the second fluid path is open in accordance with a representative embodiment of the present invention.

Referring now to FIG. 2A, a valve 200 is shown having a septum 220 in a first configuration, wherein the valve comprises a primary fluid path 210, a part of which is defined by a space between an outer surface of septum 220 and an inner wall of interior 206, and wherein valve 200 comprises a second fluid path 212, a part of which is defined by an aperture 222 of septum 220. In the first configuration, the fluid pressure threshold ($f_T$) of septum 220 is approximately equal to a first fluid pressure ($f_1$), such that septum 220 maintains a position within interior 206 that does not occlude or close primary fluid path 210. When septum 220 experiences a second fluid pressure ($f_2$) that is greater than the fluid pressure threshold of septum 220, the fluid pressure threshold is overcome and septum 220 assumes a second configuration, wherein septum 220 occludes primary fluid path 210, as shown in FIG. 2B. Unlike the embodiment shown in FIGS. 1A and 1B, the second configuration of septum 220 does not prevent all fluid flow through valve 200. Rather, the open state of the second fluid path 212 is maintained in the second configuration of septum 220.

In some instances, a clinician or other individual operating the device shown in FIG. 2B will detect a change in flow rate or fill rate when septum 220 assumes the second configuration. As such, the clinician may reduce the second fluid pressure in order to allow septum 220 to resume the first configuration. In some instances, a clinician may feel or hear the contact between septum 220 and the inner wall of interior 206 when septum 220 assumes the second configuration, which may signal the clinician to reduce the second fluid pressure.

Figure 3A:
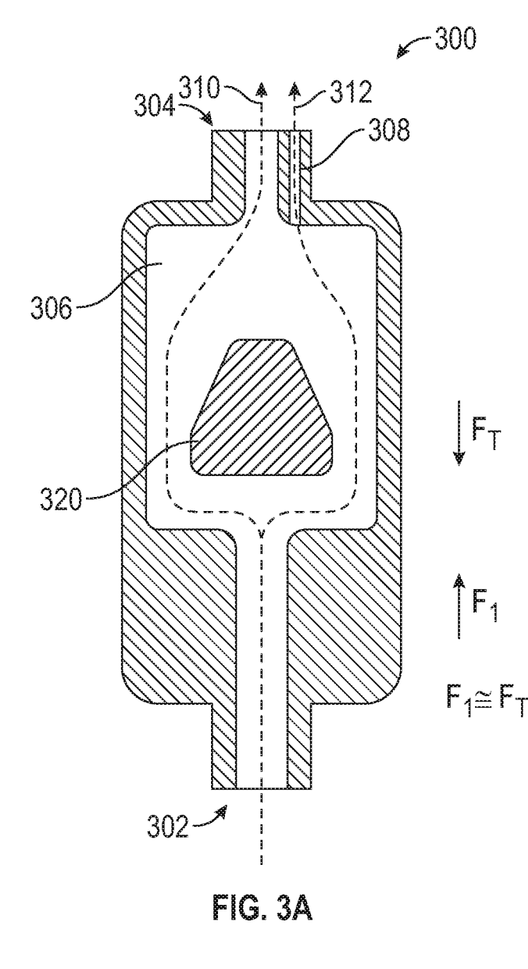
FIG. 3A is a cross-section view of a valve for controlling flow of a fluid, wherein the valve is shown in a first configuration in which a first fluid path and a second fluid path of the valve are open in accordance with a representative embodiment of the present invention.
Figure 3B:
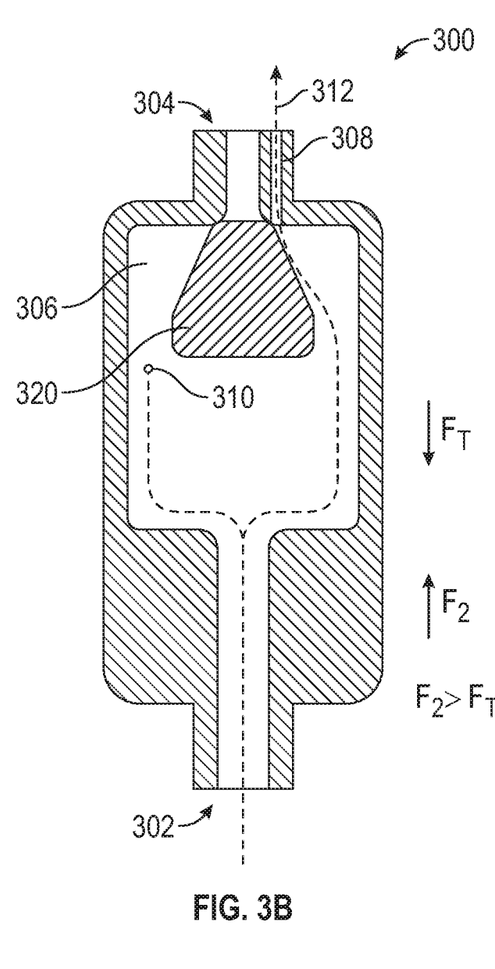
FIG. 3B is the valve of FIG. 3A, wherein the valve is shown in a second configuration in which the first fluid path is closed, and the second fluid path is open in accordance with a representative embodiment of the present invention.

Referring now to FIG. 3A, a valve 300 is shown having a septum 320 in a first configuration, wherein the valve comprises a primary fluid path 310, a part of which is defined by a space between an outer surface of septum 320 and an inner wall of interior 306, and wherein valve 300 comprises a second fluid path 312, a part of which is defined by an aperture 308 in proximity to outlet 304. In the first configuration, the fluid pressure threshold ($f_T$) of septum 320 is approximately equal to a first fluid pressure ($f_1$), such that septum 320 maintains a position within interior 306 that does not occlude or close primary fluid path 310. When septum 320 experiences a second fluid pressure ($f_2$) that is greater than the fluid pressure threshold of septum 320, the fluid pressure threshold is overcome and septum 320 assumes a second configuration, as shown in FIG. 3B. When in the second configuration, septum 320 occludes primary fluid path 310, but does not occlude the second fluid path 312. Rather, the open state of the second fluid path 312 is maintained in the second configuration of septum 320.

In some embodiments, a primary fluid path of a valve comprises a single opening or aperture in a septum. In some embodiments, a primary fluid path comprises a plurality of openings or apertures in a septum. In some embodiments, a primary fluid path comprises an aperture that is open at a fluid pressure that is equal to or less than a first fluid pressure, and that is partially closed or completely closed at a fluid pressure that is greater than a first fluid pressure.

Figure 4A:
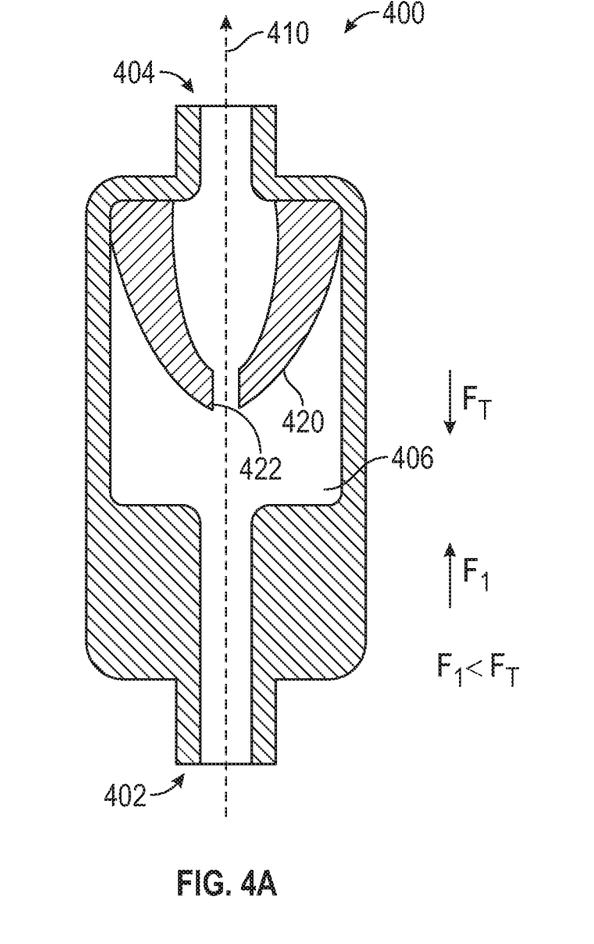
FIG. 4A is a cross-section view of a valve for controlling flow of a fluid, wherein the valve comprises a septum shown in a first configuration in which a fluid path of the valve is open in accordance with a representative embodiment of the present invention.
Figure 4B:
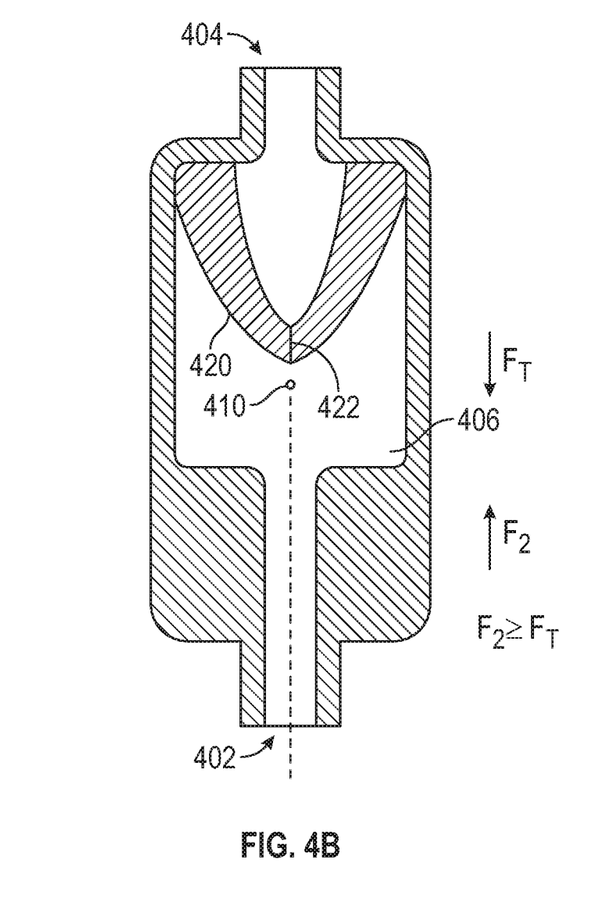
FIG. 4B is the valve of FIG. 4A, wherein the septum is shown in a second configuration by which the fluid path of the valve is closed in accordance with a representative embodiment of the present invention.

Referring now to FIG. 4A, a valve 400 is shown having a septum 420 in a first configuration, wherein the valve comprises a primary fluid path 410, a part of which is defined by an aperture 422 of septum 420. In the first configuration, the fluid pressure threshold ($f_T$) of septum 420 is greater than first fluid pressure ($f_1$), whereby aperture 422 is in an opened configuration. When aperture 422 is in an opened configuration, primary fluid path 410 is unobstructed. When septum 420 experiences a second fluid pressure ($f_2$) that is greater than or equal to the fluid pressure threshold of septum 420, septum 420 assumes a second configuration whereby aperture 422 is in a closed configuration, as shown in FIG. 4B. When in the second configuration, septum 420 occludes primary fluid path 410 such that all fluid flow through valve 400 is prevented.

In some embodiments, a septum of the present invention is configured to progressively limit a flow rate through a valve in response to increasing flow rates and/or increasing fluid pressures. Accordingly, in some embodiments a septum is configured to provide a linear response to increases in flow rates and/or fluid pressures, whereby a cross-sectional diameter of an aperture of the septum is reduced or increased relative to a change in the flow rate and/or fluid pressure experienced by the septum. In some embodiments, this is accomplished by providing a septum having a plurality of fluid pressure thresholds. In some embodiments, this is accomplished by providing a plurality of fluid pathways that are progressively closed or opened as a septum moves through a plurality of configurations linked to a plurality of fluid pressure thresholds.

Figure 5A:
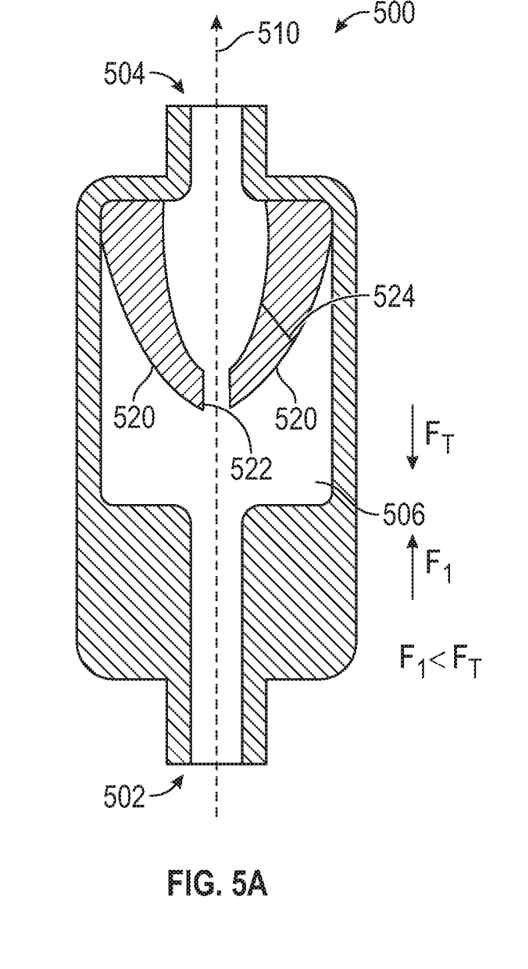
FIG. 5A is a cross-section view of a valve for controlling flow of a fluid, wherein the valve comprises a septum shown in a first configuration in which a fluid path of the valve is open, and a fluid path of the septum is closed in accordance with a representative embodiment of the present invention.
Figure 5B:
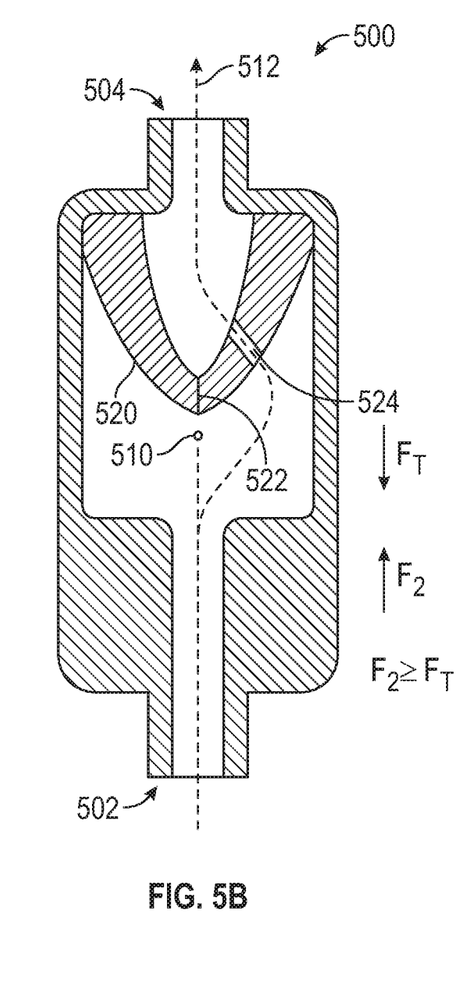
FIG. 5B is the valve of FIG. 5A, wherein the septum is shown in a second configuration by which the fluid path of the valve is closed, and the fluid path of the septum is open in accordance with a representative embodiment of the present invention.

Referring now to FIG. 5A, a valve 500 is shown having a septum 520 in a first configuration, wherein the valve comprises a primary fluid path 510, a part of which is defined by a first aperture 522 of septum 520. Septum 520 further comprises a second aperture 524. In the first configuration, the fluid pressure threshold ($f_T$) of septum 520 is greater than first fluid pressure ($f_1$), whereby aperture 522 is in an opened configuration, and second aperture 524 is in a closed configuration. When first aperture 522 is in an opened configuration, primary fluid path 510 is unobstructed. When septum 520 experiences a second fluid pressure ($f_2$) that is greater than or equal to the fluid pressure threshold of septum 520, septum 520 assumes a second configuration whereby first aperture 522 is in a closed configuration, and second aperture 524 is in an opened configuration, as shown in FIG. 5B. When in the second configuration, primary fluid path 510 is occluded, and a secondary fluid path 512 is formed through second aperture 524. In some embodiments, a flow rate through second aperture 524 is less than a flow rate through first aperture 522. As such, a clinician may detect a reduction in the flow rate and/or fill rate when septum 520 switches from the first configuration to the second configuration. In some embodiments, a change in the flow rate of valve 500 will indicate to the clinician that a change in the fluid pressure is needed in order to preserve a desired quality of a fluid flowing through valve 500.

Figure 6A:
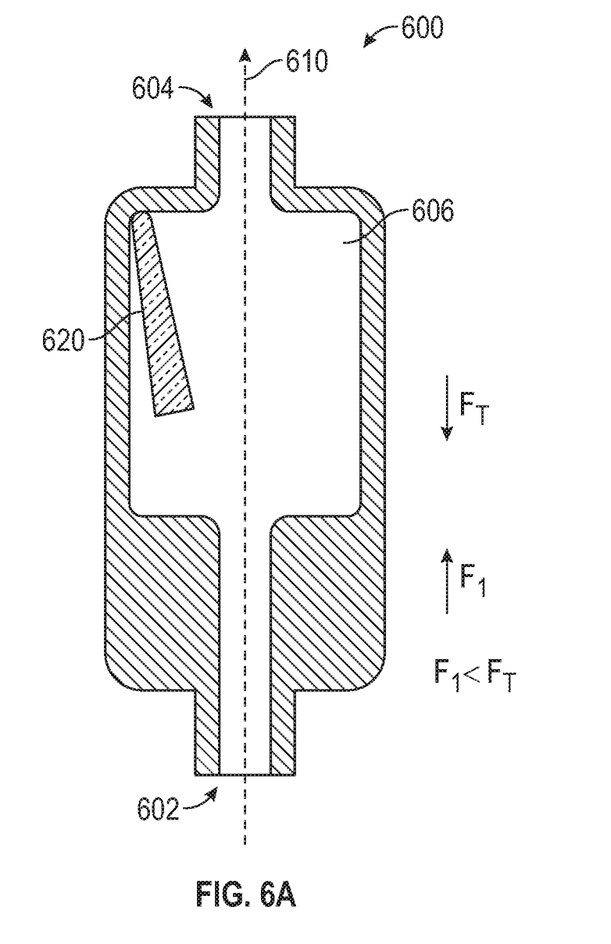
FIG. 6A is a cross-section view of a valve for controlling flow of a fluid, wherein the valve comprises a septum shown in a first configuration in which a fluid path of the valve is open in accordance with a representative embodiment of the present invention.
Figure 6B:
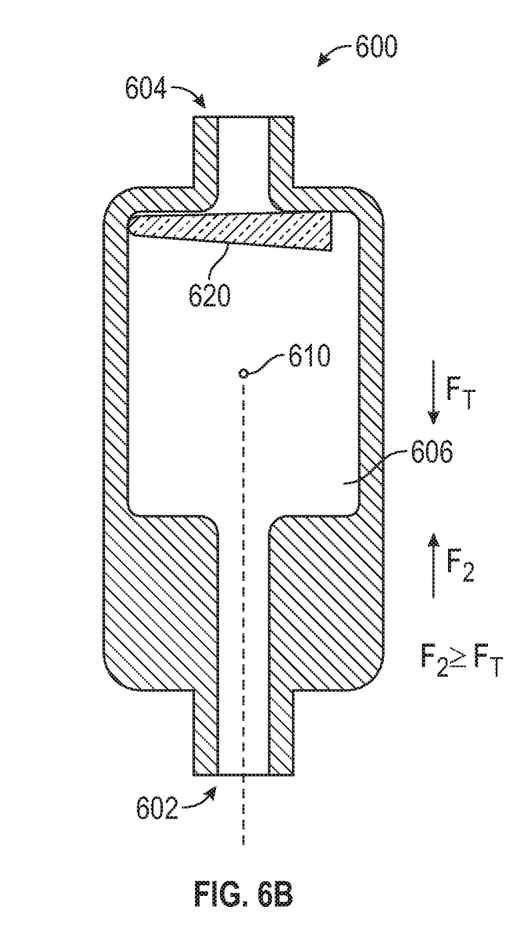
FIG. 6B is the valve of FIG. 6A, wherein the septum is shown in a second configuration by which the fluid path of the valve is closed in accordance with a representative embodiment of the present invention.

Referring now to FIG. 6A, a valve 600 is shown having a septum 620 in a first configuration, wherein the valve comprises a primary fluid path 610, a part of which is defined by a space between an outer surface of septum 620 and an inner surface of interior 606. In the first configuration, the fluid pressure threshold ($f_T$) of septum 620 is greater than first fluid pressure ($f_1$), whereby septum 620 maintains a position within interior 606 that does not occlude or close primary fluid path 610. When septum 620 experiences a second fluid pressure ($f_2$) that is greater than the fluid pressure threshold of septum 620, the fluid pressure threshold is overcome and septum 620 assumes a second configuration, wherein septum 620 occludes primary fluid path 610, as shown in FIG. 6B. In some embodiments, septum 620 is pivotally coupled to an inner surface of interior 606, such that septum 620 pivots from the first configuration to the second configuration. When in the second configuration, septum 620 occludes primary fluid path 610 such that all fluid flow through valve 600 is prevented.

Figure 7A:
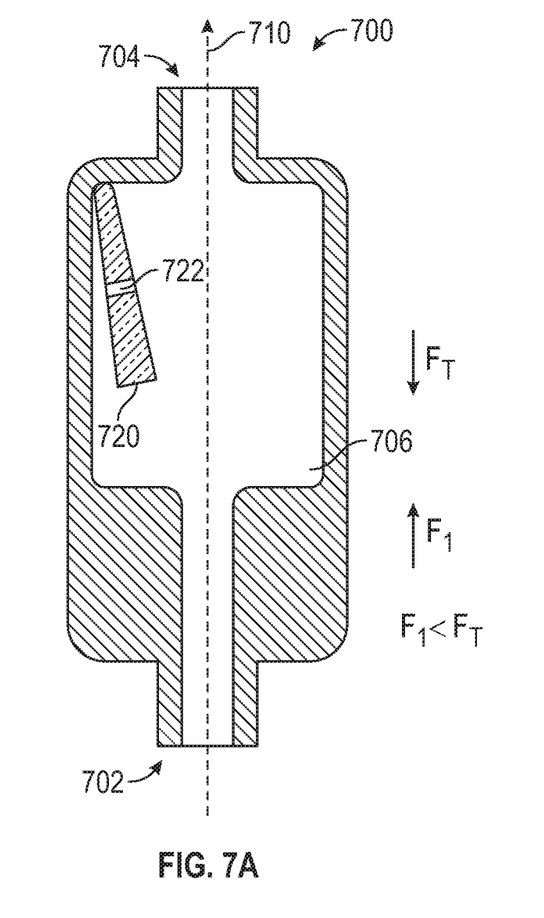
FIG. 7A is a cross-section view of a valve for controlling flow of a fluid, wherein the valve comprises a septum shown in a first configuration in which a fluid path of the valve is open, and a fluid path of the septum is open in accordance with a representative embodiment of the present invention.
Figure 7B:
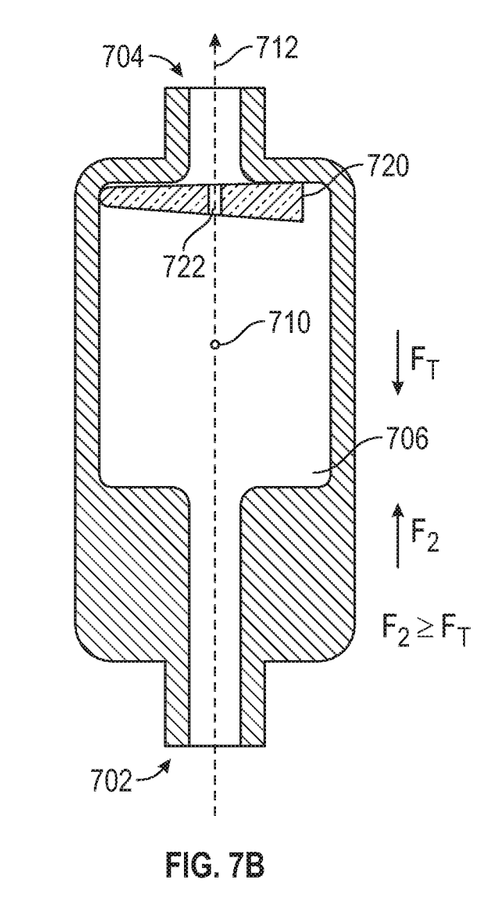
FIG. 7B is the valve of FIG. 7A, wherein the septum is shown in a second configuration by which the fluid path of the valve is reduced by the fluid path of the septum in accordance with a representative embodiment of the present invention.

Referring now to FIG. 7A, a valve 700 is shown having a septum 720 in a first configuration, wherein the valve comprises a primary fluid path 710, a part of which is defined by a space between an outer surface of septum 720 and an inner surface of interior 706. Septum 720 further comprises an aperture 722. In some embodiments, primary fluid path 710 does not include aperture 722 when septum 720 is in the first configuration. In some embodiments, primary fluid path 710 does include aperture 722 when septum 720 is in the first configuration. In the first configuration, the fluid pressure threshold ($f_T$) of septum 720 is greater than the first fluid pressure ($f_1$), whereby septum 720 maintains a position within interior 706 that does not occlude or close primary fluid path 710. When septum 720 experiences a second fluid pressure ($f_2$) that is greater than the fluid pressure threshold of septum 720, the fluid pressure threshold is overcome and septum 720 assumes a second configuration, wherein septum 720 occludes primary fluid path 710, as shown in FIG. 7B. When in the second configuration, a secondary fluid path 712 is formed through aperture 722, such that a reduced flow rate is provided through valve 700.

Figure 8A:
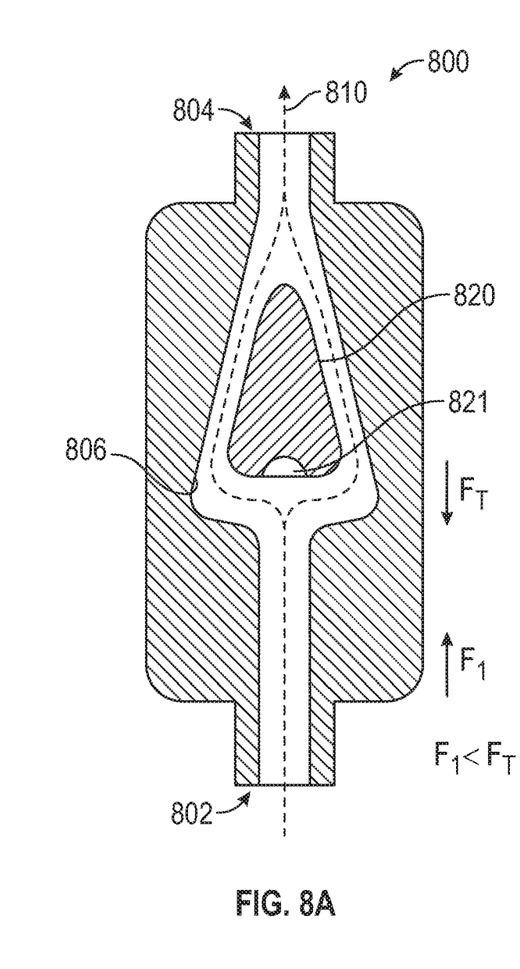
FIG. 8A is a cross-section view of a valve for controlling flow of a fluid, wherein the valve comprises a septum shown in a first configuration in which a fluid path of the valve is open in accordance with a representative embodiment of the present invention.

Referring now to FIGS. 8A to 8E, a valve 800 is shown having a conical or wedge-shaped septum 820, and a conical or wedge-shaped interior surface 806 that tapers inwardly from input 802 towards output 804, wherein the valve comprises a primary fluid path 810, a part of which is defined by a space between an outer surface septum 820 and interior surface 806. With reference to FIG. 8A, septum 820 is shown in a first configuration. In the first configuration, the fluid pressure threshold ($f_T$) of septum 820 is greater than a first fluid pressure ($f_1$), such that septum 820 maintains a position within the interior of valve 800 that does not occlude or close primary fluid path 810. In some embodiments, septum 820 comprise a structural element 821 that contributes to the fluid pressure threshold of septum 820. For example, in some embodiments septum 820 includes a structural element comprising a recessed surface configured to increase a surface area of the septum in communication with primary fluid path 810. In some embodiments, septum 820 includes a structural element configured to increase the drag of septum 820 within primary fluid path 810.

Figure 8B:
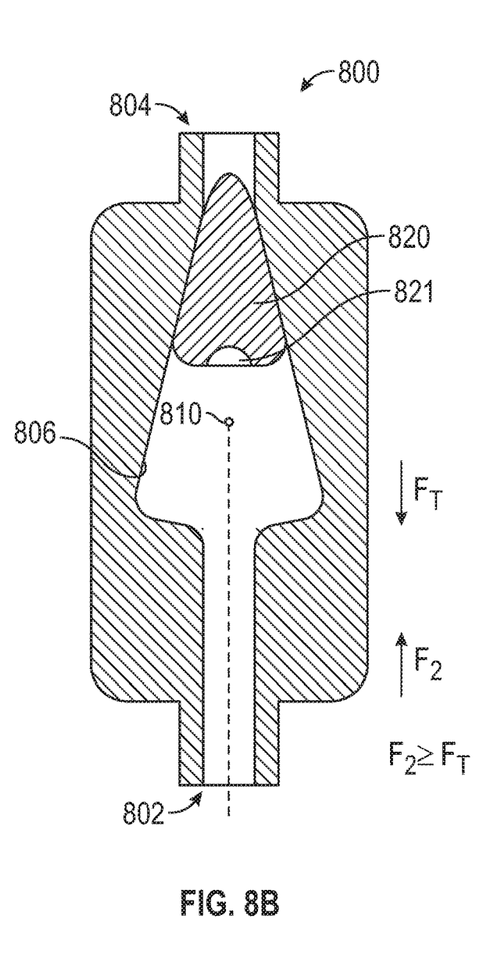
FIG. 8B is the valve of FIG. 8A, wherein the septum is shown in a second configuration by which the fluid path of the valve is closed in accordance with a representative embodiment of the present invention.

When septum 820 experiences a second fluid pressure ($f_2$) that is greater than or equal to the fluid pressure threshold of septum 820, the fluid pressure threshold is overcome and septum 820 assumes a second configuration, as shown in FIG. 8B. When in the second configuration, septum 820 forms a fluid tight seal with interior 806, whereby primary fluid path 810 is occluded such that all fluid flow through valve 800 is prevented. In some embodiments, septum 820 forms an irreversible fluid tight seal with interior 806. In other embodiments, septum 820 forms a temporary fluid tight seal with interior 806, wherein the fluid tight seal is removed when the first fluid pressure is resumed.

Figure 8C:
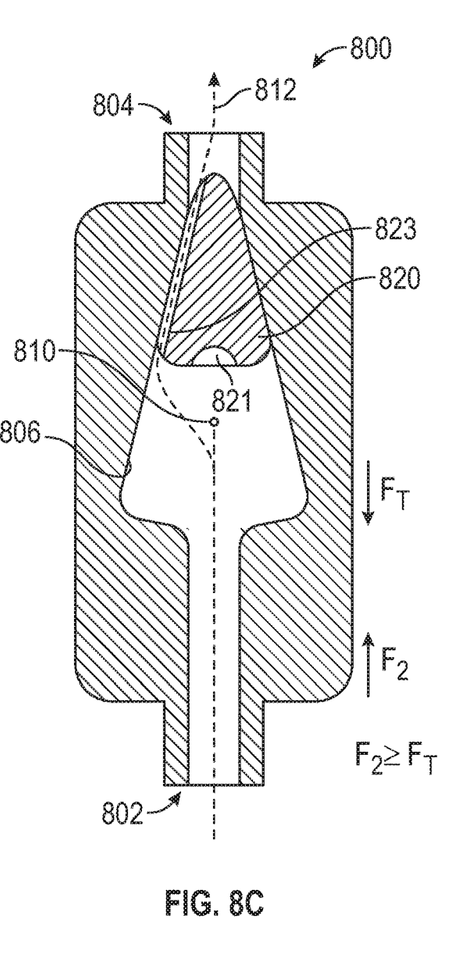
FIG. 8C is the valve of FIG. 8B, wherein the septum further comprises a fluid path that is open in accordance with a representative embodiment of the present invention.

In some embodiments, septum 820 further comprises a groove or channel 823 formed in, or otherwise provided on an outer surface of septum 820, as shown in FIG. 8C. When septum 820 is in the second configuration, channel 823 forms a secondary fluid path 812 with interior surface 806, such that a fluid may continue to flow through valve 800 via secondary fluid path 812.

Figure 8D:
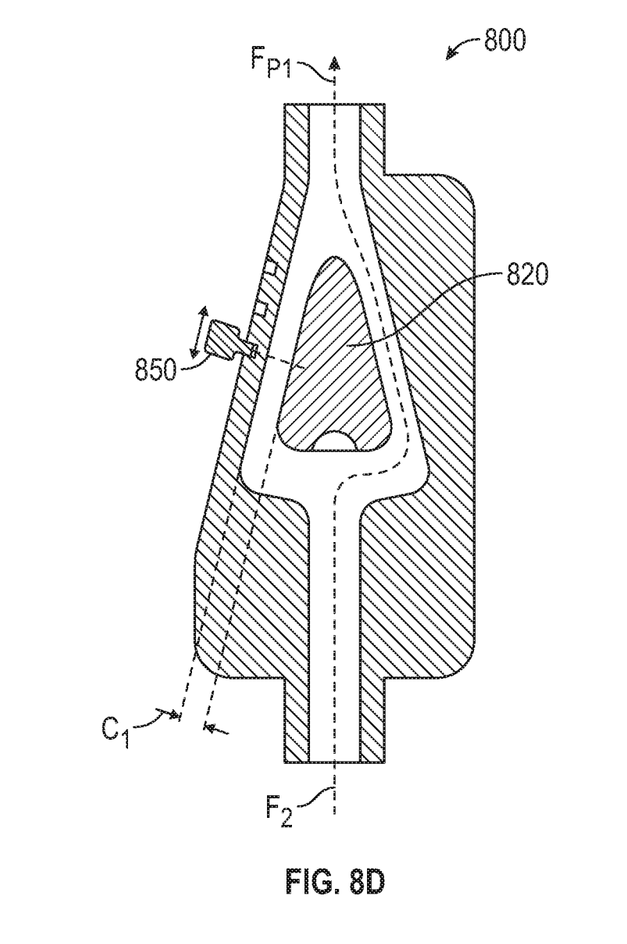
FIG. 8D is the valve of FIG. 8A further comprising means for manually adjusting a position of the septum within an interior of the valve, wherein the septum is shown in a position that allows a maximum desire flow rate of a fluid through a fluid path of the valve in accordance with a representative embodiment of the present invention.
Figure 8E:
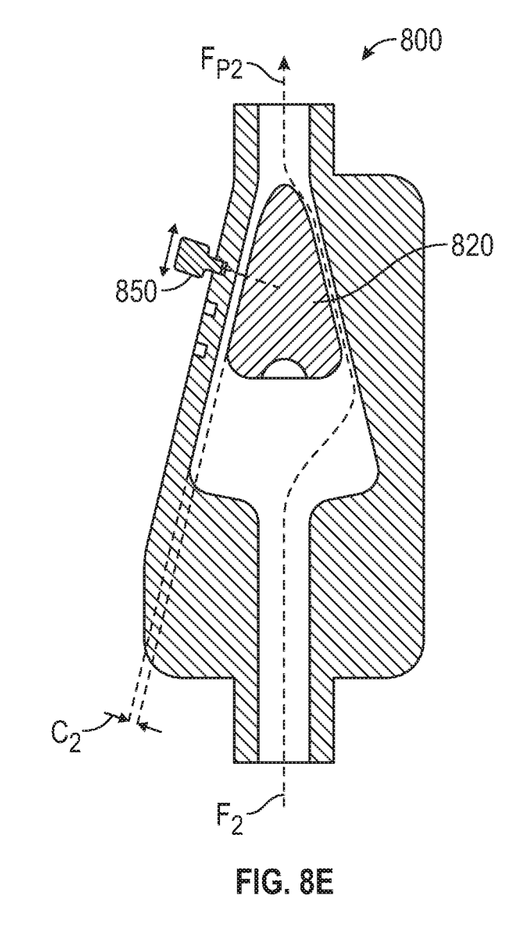
FIG. 8E is the valve of FIG. 8D, wherein the septum is shown in a position that minimizes a desired flow rate of a fluid through a fluid path of the valve in accordance with a representative embodiment of the present invention.

Referring now to FIGS. 8D and 8E, some embodiments of the present invention further comprise an external control 850 whereby a position of septum 820 may be manually selected by a clinician to achieve a preferred flow rate ($F_{p1}$ and $F_{p2}$) in response to an undesirable fluid pressure ($f_2$). External control 850 may include any features or structures whereby a clinician can manipulate and/or set a position of septum 820 within the interior of valve 800. In some embodiments, control 850 comprises a button that is operable coupled to septum 820. In some embodiments, a position of control 850 is adjustable between a plurality of set positions. In some embodiments, a position of control 850 is infinitely adjustable.

In some embodiments, the position of control 850 adjusts the volume, capacity, and/or dimensions of primary fluid path 810. As such, control 850 may increase or decrease flow through primary fluid path 810. In some embodiments, structural features of septum 820 and interior surface 806, in combination with a proximity between these surfaces determines a flow rate through valve 800. For example, as shown in FIG. 8D, the tapered, conical structures of septum 820 and interior surface 806 of valve 800 provide a first flow capacity ($C_1$) when control 850 is in a first position, wherein the first flow capacity provides a first preferred flow rate ($F_{p1}$). When control 850 is moved to a second position, a distance between the opposing surfaces of septum 820 and interior surface 806 is reduced to provide a second flow capacity ($C_2$), wherein the second flow capacity provides a second preferred flow rate ($F_{p1}$). In some embodiments, a clinician selects a position for control 850 that provides a flow rate that prevents undesired damage to a fluid flowing through valve 800.

Some embodiments of the present invention provide a valve comprising a biasing element configured to control the movement of a septum in response to fluid pressures within the valve. Biasing element may include any structure, feature or action that contributes to a position of the septum within the valve. In some instances, biasing element biases the septum towards the input end of the valve. In some embodiments, biasing element biases the septum towards the output end of the valve. In some embodiments, biasing element biases the septum towards a location that is between the input and output ends of the valve. In some embodiments, biasing element biases the septum towards an interior wall surface of the valve. In some embodiments, biasing element is a spring. In some embodiments, biasing element is a tether. In some embodiments, biasing member is deformable. In some embodiments, biasing member is resilient. In some embodiments, biasing member is flexible. In some embodiments, biasing member is rigid.

Figure 9A:
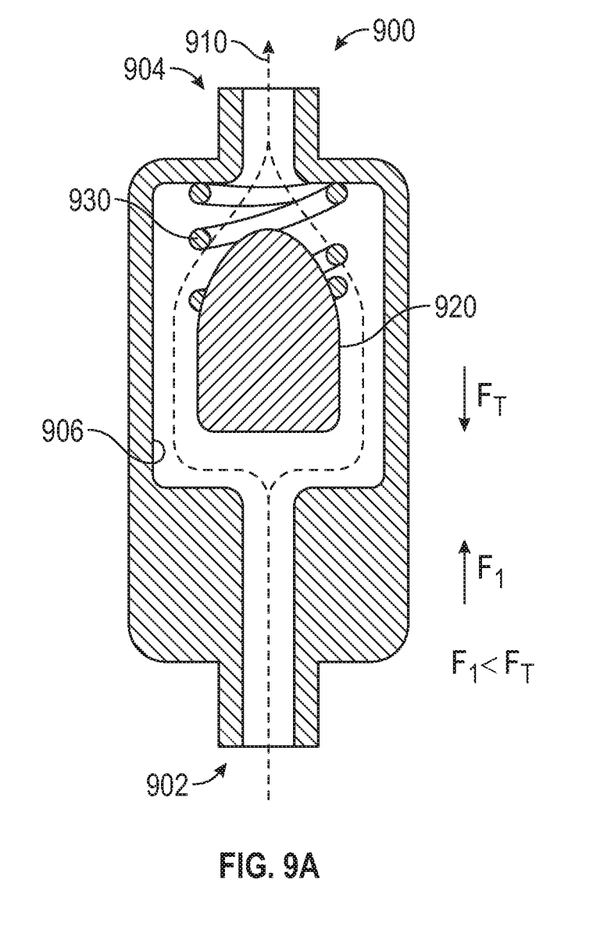
FIG. 9A is a cross-section view of a valve for controlling flow of a fluid, wherein the valve comprises a septum held in a first configuration by a biasing element, wherein a fluid path of the valve is open in accordance with a representative embodiment of the present invention.
Figure 9B:
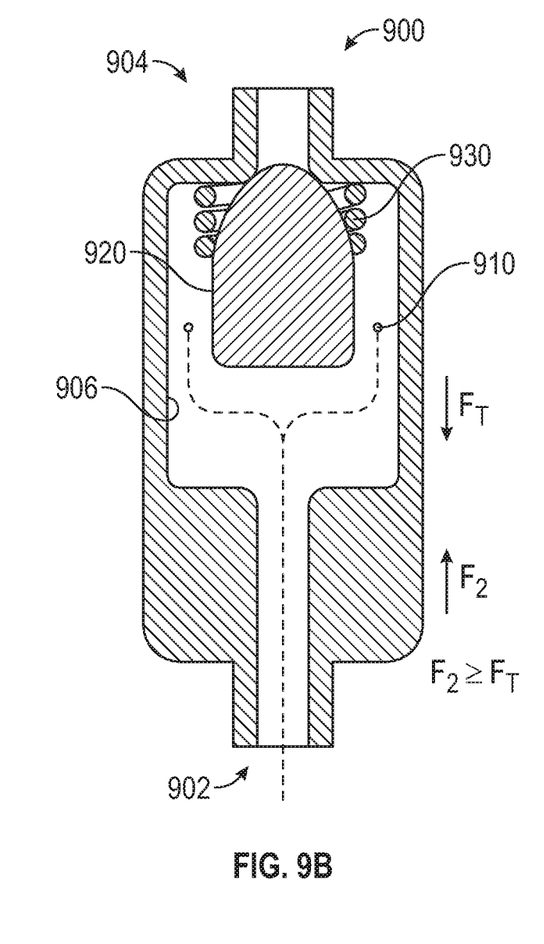
FIG. 9B is the valve of FIG. 9A, wherein the septum is shown in a second configuration by which the fluid path of the valve is closed in accordance with a representative embodiment of the present invention.

Referring now to FIG. 9A, a valve 900 is shown having a septum 920 in a first configuration, wherein the valve comprises a primary fluid path 910, a part of which is defined by a space between septum 920 and an interior surface 906 of valve 900. Valve 900 further comprises a spring biasing element 930 interposed between septum 920 and interior surface 906, wherein biasing element maintains a position of septum 920 within valve 900. In the first configuration, the fluid pressure threshold ($f_T$) of septum 920 and biasing element 930 is greater than first fluid pressure ($f_1$), whereby biasing element 930 biases septum 920 towards input end 902 to maintain a position of septum 920 that does not occlude or close primary fluid path 910. When septum 920 experiences a second fluid pressure ($f_2$) that is greater than or equal to the fluid pressure threshold of septum 920 and biasing element 930, the fluid pressure threshold is overcome and septum 920 assumes a second configuration, wherein biasing element 930 collapses and septum 920 occludes primary fluid path 910, as shown in FIG. 9B. When in the second configuration, septum 920 is moved by the second fluid pressure towards output 904 whereby septum 920 contacts output 904 and occludes primary fluid path 910, such that all fluid flow through valve 900 is prevented. In some embodiments, valve 900 may include secondary fluid paths which provide limited fluid flow through valve 900 when septum 920 is in the second configuration.

Figure 10A:
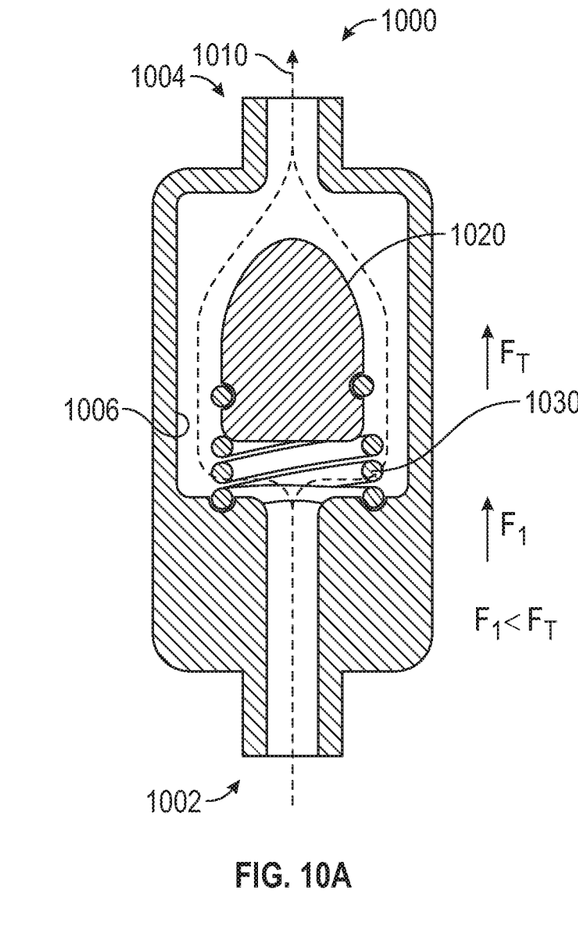
FIG. 10A is a cross-section view of a valve for controlling flow of a fluid, wherein the valve comprises a septum held in a first configuration by a biasing element, wherein a fluid path of the valve is open in accordance with a representative embodiment of the present invention.
Figure 10B:
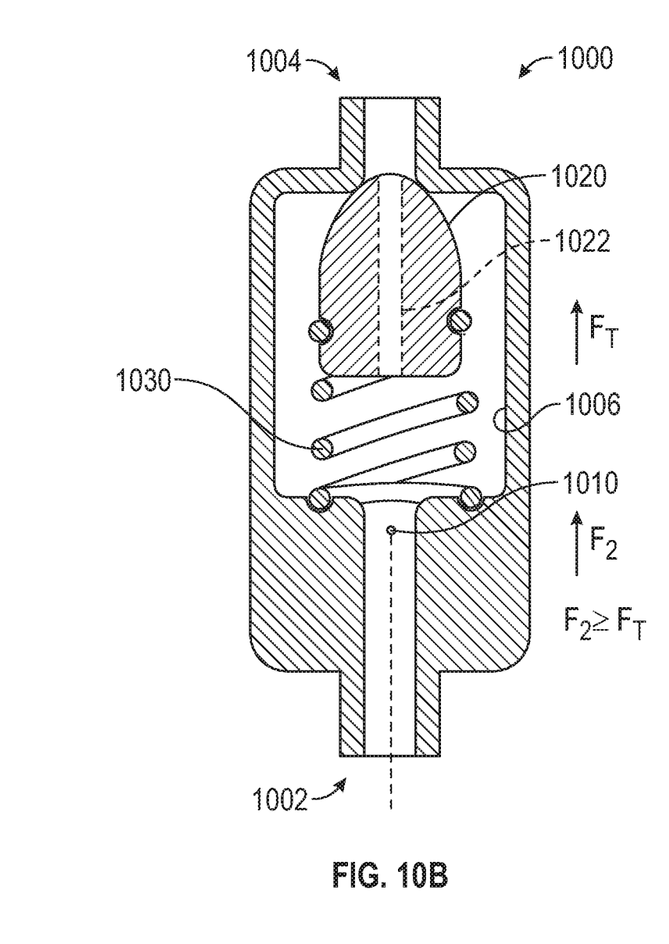
FIG. 10B is the valve of FIG. 10A, wherein the septum is shown in a second configuration by which the fluid path of the valve is closed, and wherein the septum is shown with a alternative fluid path in accordance with one or more representative embodiments of the present invention.

Referring now to FIG. 10A, a valve 1000 is shown having a septum 1020 in a first configuration, wherein the valve comprises a primary fluid path 1010, a part of which is defined by a space between septum 1020 and an interior surface 1006 of valve 1000. Valve 1000 further comprises a spring biasing element 1030 interposed between septum 1020 and interior surface 1006, wherein biasing element maintains a position of septum 1020 within valve 1000. In the first configuration, the fluid pressure threshold ($f_T$) of septum 1020 and biasing element 1030 is greater than first fluid pressure ($f_1$), whereby biasing element 1030 biases septum 920 away from input 1002 and towards output 1004, to a position that does not occlude or close primary fluid path 1010. When septum 1020 experiences a second fluid pressure ($f_2$) that is greater than or equal to the fluid pressure threshold of septum 1020 and biasing element 1030, the fluid pressure threshold is overcome and septum 1030 assumes a second configuration, whereby biasing element stretches an septum 1020 occludes primary fluid path 1010, as shown in FIG. 10B. When in the second configuration, septum 1020 is moved by the second fluid pressure towards output 1004 whereby septum 1020 contacts output 1004 and occludes primary fluid path 1010, such that all fluid flow through valve 900 is prevented. In some embodiments, valve 1000 may include a secondary fluid path 1022 which provides limited fluid flow through valve 1000 when septum 1020 is in the second configuration.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A valve for controlling flow of a fluid, said valve comprising:
    an enclosure comprising an inlet and an outlet;
    a primary fluid path; and
    a septum positioned within an interior of the enclosure, the septum comprising a first configuration at a first fluid pressure within the interior, and a second configuration at a second fluid pressure within the interior,
    wherein the septum comprises a first aperture defining a part of the primary fluid path and a second aperture defining a secondary fluid path,
    wherein the primary fluid path is unobstructed when the septum is in the first configuration, and obstructed when the septum is in the second configuration,
    wherein the secondary fluid path is unobstructed by the septum in the second configuration, and
    wherein the primary fluid path comprises a primary flow rate capacity that is greater than a secondary flow rate capacity of the secondary fluid path.

2. The valve of claim 1, wherein the septum further comprises a fluid pressure threshold at which the septum switches from the first configuration to the second configuration.

3. The valve of claim 2, wherein the first configuration is an opened configuration, and the first fluid pressure is equal to, or less than the fluid pressure threshold, and the second configuration is a closed configuration, and the second fluid pressure is greater than the fluid pressure threshold.

4. The valve of claim 2, wherein the fluid pressure threshold is a fluid vacuum pressure threshold, the first fluid pressure is a first fluid vacuum pressure, and the second fluid pressure is a second fluid vacuum pressure.

5. The valve of claim 4, wherein the first configuration is an open configuration, and the first fluid vacuum pressure is less than or equal to the fluid vacuum pressure threshold of the septum, and the second configuration is a closed configuration, and the second fluid vacuum pressure is greater than the fluid vacuum pressure threshold.

6. The valve of claim 1, wherein contact between opposing surfaces of the septum obstructs the primary fluid path.

7. The valve of claim 1, wherein the septum is fixedly positioned within the interior.

* * * * *